United States Patent
Hayami et al.

(10) Patent No.: US 7,136,582 B2
(45) Date of Patent: Nov. 14, 2006

(54) LIGHTING APPARATUS

(75) Inventors: Kenichi Hayami, Tokyo (JP); Masaaki Kaneko, Tokyo (JP)

(73) Assignee: TDK Corporation, Tokyo (JP)

( * ) Notice: Subject to any disclaimer, the term of this patent is extended or adjusted under 35 U.S.C. 154(b) by 180 days.

(21) Appl. No.: 10/921,843

(22) Filed: Aug. 20, 2004

(65) Prior Publication Data

US 2005/0047772 A1 Mar. 3, 2005

(30) Foreign Application Priority Data

Aug. 28, 2003 (JP) .............................. 2003-304434

(51) Int. Cl.
*G03B 15/03* (2006.01)
*H04N 5/222* (2006.01)

(52) U.S. Cl. .................. 396/182; 396/199; 362/11; 348/370

(58) Field of Classification Search ............... 396/155, 396/182, 199; 362/3, 11; 348/370, 371
See application file for complete search history.

(56) References Cited

U.S. PATENT DOCUMENTS

| 5,010,412 A * | 4/1991 | Garriss ...................... 348/371 |
| 5,450,291 A * | 9/1995 | Kumagai ....................... 362/3 |
| 6,454,437 B1 * | 9/2002 | Kelly ......................... 362/246 |
| 6,554,452 B1 * | 4/2003 | Bourn et al. .................. 362/247 |
| 6,749,310 B1 * | 6/2004 | Pohlert et al. .................. 362/11 |
| 6,929,375 B1 * | 8/2005 | Satomi ......................... 362/11 |
| 2003/0030745 A1 * | 2/2003 | Meek et al. .................... 362/11 |
| 2005/0057184 A1 * | 3/2005 | Kaneko et al. ............. 315/247 |
| 2005/0156531 A1 * | 7/2005 | Young ......................... 315/112 |

FOREIGN PATENT DOCUMENTS

| JP | 02-244685 | 9/1990 |
| JP | 06-222427 | 8/1994 |
| JP | 10-206237 | 8/1998 |
| JP | 10-312450 | 11/1998 |
| JP | 2000-337967 | 12/2000 |
| JP | 2001-043728 | 2/2001 |
| JP | 2001-242553 | 9/2001 |
| JP | 2002-101274 | 4/2002 |
| JP | 3-92897 | 1/2003 |

* cited by examiner

*Primary Examiner*—W. B. Perkey
(74) *Attorney, Agent, or Firm*—Oblon, Spivak, McClelland, Maier & Neustadt, P.C.

(57) ABSTRACT

The present invention aims at providing a lighting apparatus which is to be installed in a color camera, which is capable of providing the stable quantity of light from a light source such as an LED, and which is capable of stabilizing color tones of an image captured with the color camera. In order to attain this object, in the lighting apparatus according to the present invention, the temperature control for the camera is also simultaneously carried out using a thermal transfer member for enhancing heat transfer between a Peltier element used for the temperature control for an LED case with built-in LEDs, and the LED case.

5 Claims, 4 Drawing Sheets

LIGHTING APPARATUS

BACKGROUND OF THE INVENTION

1. Field of the Invention

The present invention relates in general to a lighting apparatus constituted by light emitting elements such as light emitting diodes. In particular, the present invention relates to a lighting apparatus which has such a simple construction as to be easily detached from and attached to a camera or the like, and which is capable of providing a stable luminous intensity independently of a change in temperature of light emitting elements.

2. Related Background Art

For example, there is known an inspection apparatus for photographing an object of inspection using a camera to carry out the quality control of the object based on the photography results. In such an inspection apparatus, in order to make an image of the object clearer, a lighting apparatus for lighting up an object is also simultaneously used. For this lighting apparatus, there is used one having a plurality of light emitting diodes (hereinafter referred to as "LEDs" for short when applicable) used therein because the LED has essentially the high directivity and hence does not require a reflecting plate or the like, and is miniature and has a low power consumption, and so forth.

However, the LED has the characteristics that a temperature thereof changes in correspondence to the use situation, and the quality of light thereof also changes in correspondence to the change in temperature. More specifically, the LED has a problem that when the temperature thereof rises, the quantity of light thereof decreases, and, for example, after the quantity of light becomes temporarily stable after the LED has been turned ON, the temperature rises with a lapse of the lighting time to decrease the quantity of light. For this reason, in the usual way, those LEDs are used while their temperatures are controlled by a temperature measurement device and a cooling device such as a Peltier element which are disposed in the vicinities of the LEDs. Exemplifications of such a construction are disclosed in Japanese Patent Application Laid-Open No. 2002-101274, Japanese Patent Application Laid-Open No. 2001-043728 and Japanese Patent Application Laid-Open No. 2000-337967, for example.

Examples of the above-mentioned inspection apparatus include an apparatus for visual inspection of semiconductor products (refer to Japanese Patent Application Laid-Open No. 10-206237, for example) and an apparatus for recognizing a shape of an article (refer to Japanese Patent Application Laid-Open No. 10-312450, for example). In such an apparatus, light having high directivity is applied to an object to photograph the object which is made clear by reflection of the light, and the inspection results, the shape recognition results, or the like are obtained based on the photography results. Possible objects of photography include one in which chips or the like are mounted on a circuit board. In the photography of such an object, in order to cope with the miniaturization of chips, the promotion of high density of a mounting state, and the like, in recent years, there is required a combination of a light source which can have higher directivity and provide the stable quantity of light, and a camera having high sensitivity or a camera with which color photography can be carried out.

In an inspection apparatus used in an inspection process for high density mounting electronic components obtained through the multikind and small-quantity production process, it is necessary to photograph clear images of various kinds of boards and mounting chips which are different in height, size, reflectivity, color tone, and the like, combinations thereof, and the like. Even when such a lighting apparatus changes in lighting state for an object, the quantity of change in lighting state has not become a problem in the normal photographing conditions up to this day, or the photography or the like has been carried out under a condition in which the quantity of change does not become a problem. However, for example, in the case where an electronic component is inspected for mounting state, when the electronic component, the mounting board, and the like are further miniaturized, and also the color tones or the like in their materials become close to each other, the above-mentioned change in lighting state may become unable to be disregarded.

For this reason, it is required that focal points of a lighting apparatus and a camera be readily and speedily changed, and lighting rays be applied to an object of the photography with the nearly equal quantities of rays and from nearly equal directions to obtain an image. It is conceivable that such a request will become more and more severe in the future along with the miniaturization and promotion of high performance of the electronic components. In addition, it is also supposed that when the camera and the lighting apparatus are miniaturized and the camera and the lighting apparatus are then tried to be easily detached from and attached to each other, the disposition itself of a temperature measurement device within the lighting apparatus becomes difficult.

In addition, in order to photograph and analyze an object of the photography which is more difficult in resolution, there is also used a camera for capturing an image in the color style. In the usual way, in such a camera, colors of an image are extracted based on a difference in radiation temperature between an object and the black body. For this reason, when a temperature of a camera itself rises due to the heat conduction from the LEDs or the radiation heat from the LEDs, there is a possibility that although there is a single object of the photography, the color of the resultant image differs from part to part of the image. Even if this color change does not become a problem in the current use situation, when an object of the photography is miniaturized and complicated, it is required to construct a photography system which takes that color change into consideration.

In the usual way, a focal point of a camera can be readily adjusted by driving a built-in lens of the camera. However, when a lighting apparatus constituted by a plurality of LEDs each having high directivity is used as a light source, it is normally difficult to move a focal point of the lighting apparatus. In addition, when it is required to change a luminescent color of an LED, normally, a filter or the like is forced to be disposed in front of the LED to cope with that request. Examples of a normally conceivable coping method include a method involving: preparing in advance a plurality of kinds of lighting apparatuses having different focal lengths; and fixing any one of these lighting apparatuses to a camera in correspondence to an application. Examples of the construction of the lighting apparatus include ones disclosed in Japanese Patent Application Laid-Open No. 2001-043728 and Japanese Patent Application Laid-Open No. 2000-337967.

As described above, however, in order to obtain the stable quantity of light from an LED, the LED needs to be used under the environmental conditions having a fixed temperature. For this reason, as described in Japanese Patent Application Laid-Open No. 2001-043728 etc., the lighting apparatus needs to be provided with a thermometer, a Peltier element as a cooling device, and a control system for the thermometer and the Peltier element. Hence, it is judged that in actual, this lighting apparatus will require a complicated wiring and the like. Consequently, when any one of the lighting apparatuses disclosed in the above-mentioned Patent Documents is tried to be installed in an actual camera, it is judged to be difficult to carry out an operation for the installation readily and speedily.

In addition, Japanese Patent Application Laid-Open No. 2002-101274 mentioned above discloses a construction in which an LED, a Peltier element, and a heat radiating plate are provided integrally with one another. Japanese Patent Application Laid-Open No. 2002-101274 also discloses the contents in which for the maintenance or the like, those constituent elements can be separated from one another. However, the construction disclosed in Japanese Patent Application Laid-Open No. 2002-101274 permits the constituent elements to be separated from one another only for the maintenance. Thus, for example, it is judged that this construction is not suitable for a situation in which an LED is frequently exchanged for another one. In addition, with the constructions disclosed in the above-mentioned Patent Documents, it is judged to be difficult to reduce a change in temperature which is generated in a camera or the like having the LEDs fixed thereto due to the fixing of the LEDs or the like.

SUMMARY OF THE INVENTION

The present invention has been made in the light of the above-mentioned circumstances, and it is, therefore, an object of the present invention to provide a construction permitting light emitting diodes and the like used in a lighting apparatus to be readily detached from and attached to a camera. It is another object of the present invention to provide a lighting unit or apparatus which has a construction permitting light emitting diodes and the like to be readily detached and attached from and to a camera, and which is capable of adjusting a temperature of an object, such as a camera, having the lighting apparatus fixed thereto.

In order to solve the above problems, according to one aspect of the present invention, there is provided a lighting unit fixed to an object to have the lighting unit installed therein for lighting up the vicinity of a predetermined focal point, the lighting unit including: a light emitting diode case having an accommodation space vertically formed and adapted to accommodate the object to have the lighting unit installed therein, and a lower end surface to which a plurality of light emitting diodes able to apply light to the predetermined focal point are fixed; a temperature control element having an accommodation space vertically formed and adapted to accommodate the object to have the lighting unit installed therein, and a lower end surface adapted to be brought into tight contact with an upper end surface of the light emitting diode case; and a heat radiating member having an accommodation space vertically formed and adapted to accommodate the object to have the lighting unit installed therein, a lower end surface adapted to be brought into tight contact with an upper end surface of the temperature control element, and an upper end surface having a heat radiating construction formed therein, the light emitting diode case, the temperature control element, and the heat radiating member being independent of one another, the lighting unit further including: a fixing member for being urged to at least one of the light emitting diode case and the heat radiating member by an elastic portion, and for contacting the other of the light emitting diode case and the heat radiating member to urge the other in a direction of the one to bring the light emitting diode case, the temperature control element, and the heat radiating member into tight contact with one another when the light emitting diode case, the temperature control element, and the heat radiating member are assembled integrally with one another.

In further aspect of the lighting unit, it is preferable that a thermal transfer member be disposed in the accommodation space of at least the temperature control element to contact an end portion of the temperature control element on a side of the accommodation space, and a surface of the object to have the lighting unit installed therein. In further aspect of the lighting unit, it is preferable that one end portion of the fixing member be fixed to at least one of the light emitting diode case and the heat radiating member through a member having the elastic portion, the other end portion of the fixing member have a contact surface having a predetermined angle with respect to a vertical direction, and the contact surface contact a recess portion provided in the other end portion or an outer periphery of the light emitting diode case to thereby apply a vertical urging force to the recess portion. In further aspect of the lighting unit, it is preferable that the light emitting diode case have a protection circuit connected to the light emitting diode.

In order to solve the above problems, according to another aspect of the present invention, there is provided a lighting apparatus fixed to an object to have the lighting apparatus installed therein for lighting up the vicinity of a predetermined focal point, the lighting apparatus including: a light emitting diode case having an accommodation space vertically formed and adapted to accommodate the object to have the lighting apparatus installed therein, and a lower end surface to which a plurality of light emitting diodes able to apply light to the predetermined focal point are fixed; a temperature control element having an accommodation space vertically formed and adapted to accommodate the object to have the lighting apparatus installed therein, and a lower end surface adapted to be brought into tight contact with an upper end surface of the light emitting diode case; and a thermal transfer member disposed in the accommodation space of at least the temperature control element to contact an end portion of the temperature control element on a side of the accommodation space, and a surface of the object to have the lighting apparatus installed therein.

In the lighting unit according to the present invention, the light emitting diode case having a plurality of light emitting diodes fixed thereto, a Peltier element, and a heat radiating member are readily fixed to a camera as an object to have the lighting unit fixed thereto using a fixing member to allow the individual constituent elements to be brought into tight contact with one another. Consequently, when a height of an object to be photographed changes, when a color tone changes, when a light source having a plurality of focal points is required, and so forth, the case and all having the light emitting diodes fixed thereto can be readily exchanged as a dedicated lighting apparatus for another one. In addition, the Peltier element also becomes easy to be exchanged for another one in correspondence to its cooling efficiency. Hence, the general purposability is remarkably enhanced in terms of the lighting unit. In addition, in the present invention, a protection unit, for the light emitting diode, constituted by a temperature fuse, a thermostat, or the like is disposed in the light emitting diode case to reduce the number of wirings distributed among the constituent elements to thereby simplify the construction.

In addition, in the lighting apparatus according to the present invention, a temperature of a camera as an object to have the lighting apparatus installed therein is also simultaneously controlled using a Peltier element. The light emitting diodes, the camera, and the like are made a thermally integral system to be brought into tight contact with the Peltier element through a heat transfer member. Thereby, the temperature of the camera can be held constant, and even when a color camera is used, an image having a fixed color tone can be obtained. In addition, with this construction, it is also possible to raise the temperatures of the light emitting diodes, the camera, and the like at the beginning of an operation of the camera and the like using the Peltier element. Hence, it is also possible to obtain an effect of shortening a time period required to activate the installation itself.

DETAILED DESCRIPTION OF THE PREFERRED EMBODIMENTS

Figure 1:
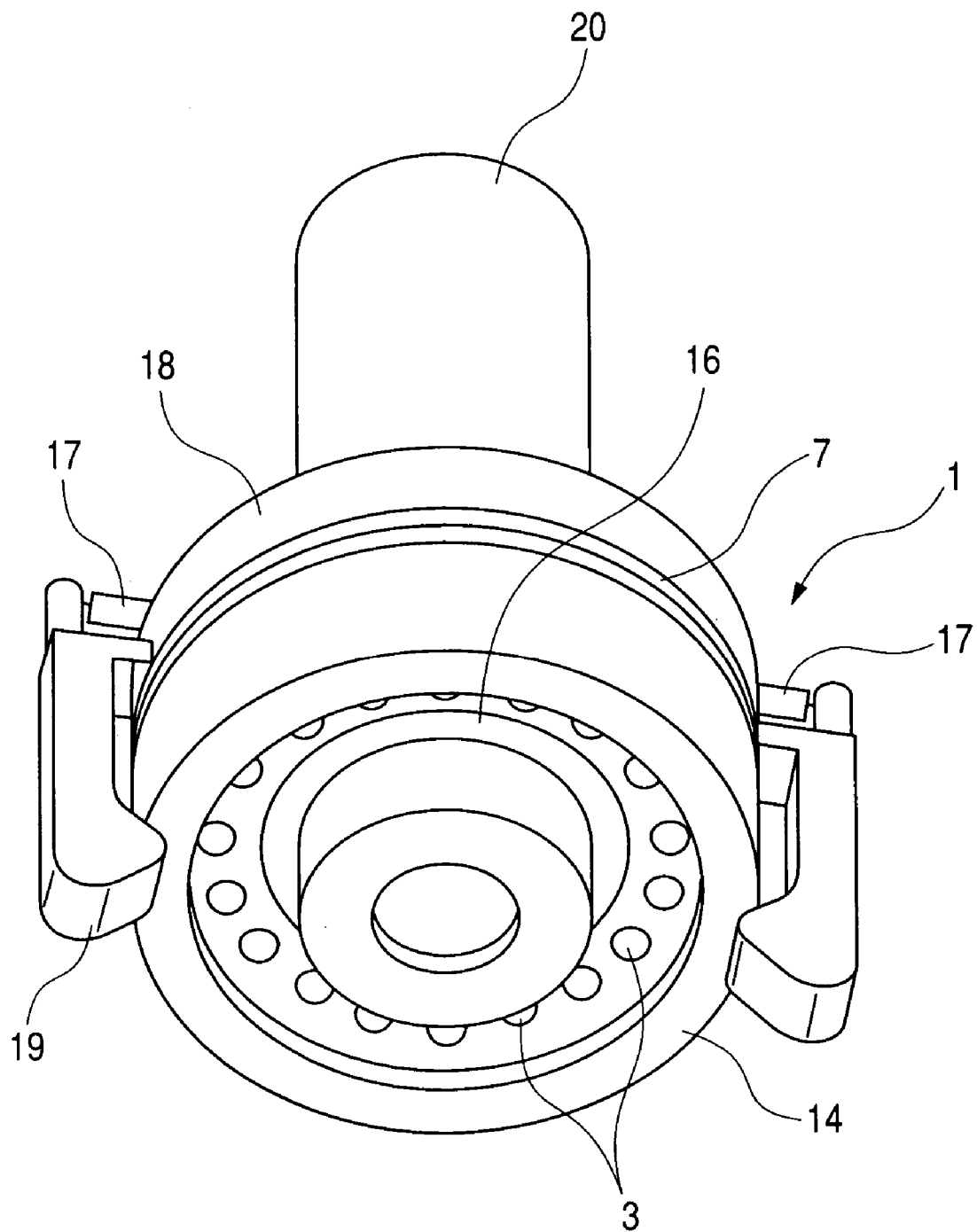
FIG. 1 is a perspective view showing a schematic construction of a camera in which a lighting apparatus according to an embodiment of the present invention is installed.
Figure 2:
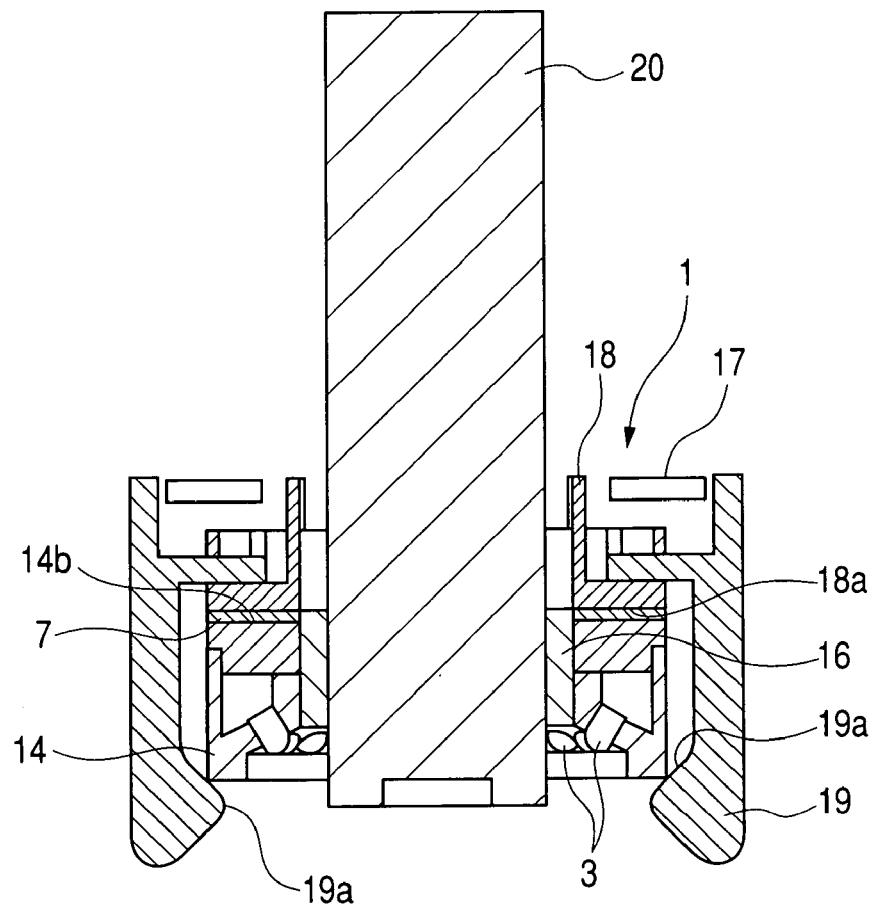
FIG. 2 is a cross sectional view showing a schematic cross section of the construction shown in FIG. 1.

A preferred embodiment using a lighting apparatus according to the present invention will hereinafter be described in detail with reference to the accompanying drawings. FIG. 1 is a schematic perspective view in a state in which a lighting apparatus according to the present invention is constructed in the form of a unit to be installed in a camera. FIG. 2 shows a schematic cross section of the construction shown in FIG. 1. The lighting apparatus 1 has a nearly ring like shape, and a camera 20 is inserted into a through hole portion (accommodation space) of the lighting apparatus 1. In addition, the lighting apparatus 1 has a ring like light emitting diode (LED) case 14 to which a plurality of LEDs 3 are fixed so as to be directed downwardly, and a ring like Peltier element 7 brought into tight contact with a rear surface of the LED case 14.

A cylindrical thermal transfer member 16 which is also brought into tight contact with the Peltier element 7 is tightly fixed to an inner peripheral portion of the through hole, as the accommodation space, of the LED case 14. The camera 20 is provided so as to extend completely through the through hole in a state of being brought into tight contact with the thermal transfer member 16, and is held at the same temperature as that of the LED case 14 through the thermal transfer member 16. In addition, a heat radiating plate 18 is mounted to a surface of the Peltier element 7 opposite to the tightly contacting surface with the LED case 14 to thereby enhance the cooling efficiency of the Peltier element 7. The LEDs 3 and the Peltier element 7 are connected to respective power sources (not shown) and respective measurement systems (not shown). Thus, the temperatures of the LEDs 3, the Peltier element 7, and the camera 20 are held at nearly fixed values, respectively.

One end portion of an elastic member 17 having a spring is fixed to an upper end portion of the heat radiating plate 18. The other end portion of the elastic member 17 is fixed to an upper end portion of a fixing member 19. Formed in a lower end portion of the fixing member 19 is a contact surface 19a which has a predetermined angle with respect to a vertical direction and which is provided so as to be directed upwardly in a through hole direction. Thus, the contact surface 19a is adapted to contact a lower end portion of an outer periphery of the LED case 14. The fixing member 19 is urged towards the through hole by the elastic member 17, and hence the contact surface 19a is brought into contact with the lower end surface of the outer periphery of the LED case 14 to urge the LED case 14 upwardly, i.e., in a heat radiating plate direction. As a result, the LED case 14, the Peltier element 7, and the heat radiating plate 18 are brought into tight contact with one another to be able to operate in the form of an integral one unit.

Figure 3A:
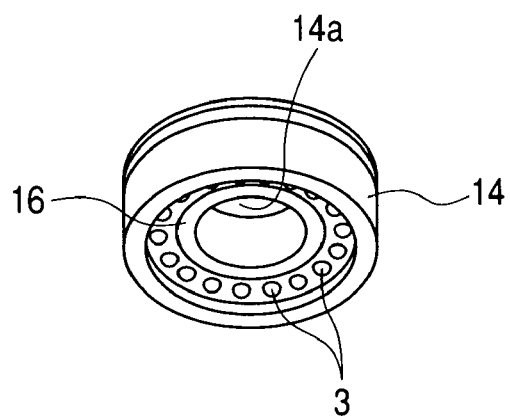
FIG. 3A is a perspective view showing details of a light emitting diode (LED) case shown in FIG. 1.
Figure 3B:
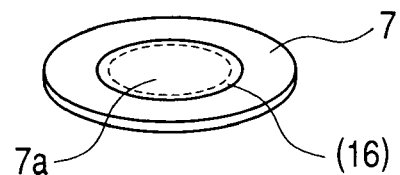
FIG. 3B is a perspective view showing details of a Peltier element shown in FIG. 1.
Figure 3C:
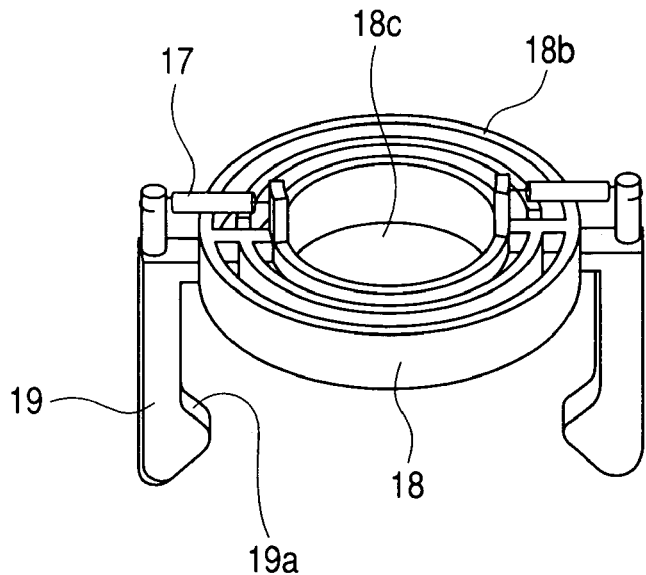
FIG. 3C is a perspective view showing details of a heat radiating plate shown in FIG. 1.

Next, the LED case 14, the Peltier element 7, and the heat radiating plate 18 which are used in this embodiment will hereinafter be described in detail with reference to FIGS. 3A to 3C. FIGS. 3A to 3C show perspective views of the LED case 14, the Peltier element 7, and the heat radiating plate 18, respectively. The LED case 14 has a flat surface 14b which is to be brought into tight contact with a lower surface of the Peltier element 7 in an upper surface of the case, and has a plurality of LEDs 3 which are disposed in a ring like shape so as to have a common focal point in a predetermined position in a low surface of the case. In addition, an accommodation space 14a into which the camera 20 is to be inserted is formed in a nearly central portion of the LEDs 3 disposed in a ring like shape. Note that the nearly cylindrical thermal transfer member 16 is disposed in the accommodation space 14a, and an outer peripheral portion of the thermal transfer member 16 is brought into tight contact with an inner peripheral portion of the LED case 14 on a side of the accommodation space 14a.

The Peltier element 7 has a ring like shape, and also has an accommodation space 7a into which the camera 20 is to be inserted in an inside thereof. The above-mentioned thermal transfer member 16 extends up to the accommodation space 7a, and hence is brought into tight contact with an inner peripheral portion as well of the Peltier element 7 on a side of the accommodation space 7a. It should be noted that an outer diameter of the camera 20 inserted into the through hole of the nearly cylindrical thermal transfer member 16 is nearly equal to an inner diameter of the through hole of the thermal transfer member 16. Thus, when the camera 20 is inserted into the through hole of the lighting apparatus 1, an outer peripheral portion of the camera 20 is brought into tight contact with the inner peripheral portion of the thermal transfer member 16.

The heat radiating plate 18 has a flat surface 18a to be brought into tight contact with the upper surface of the Peltier element 7 in a lower surface of the plate, and has a heat sink 18b in an upper surface of the plate. Although the heat radiating plate 18 also has an accommodation space 18c into which the camera 20 is to be inserted, the thermal transfer member 16 does not extend up to the accommodation space 18c. The heat radiating plate 18 has a function for radiating the heat discharged from the Peltier element 7 into the space, and hence must be thermally insulated from the thermal transfer member 16. Consequently, when the heat radiating plate 18 is disposed close to the thermal transfer member 16, a heat insulating member is preferably disposed between the thermal transfer member 16 and the heat radiating plate 18.

In this embodiment, one end of the spring 17 is fixed to an upper end portion of the heat sink 18b, and the other end of the spring 17 is connected to the upper end portion of the fixing member 19 as described above. The fixing member 19 extends vertically, and has the contact surface 19a which is formed so as to be directed upwardly in the accommodation space direction in a lower end portion of the fixing member. The fixing member 19 is adapted to be driven in the accommodation space direction (horizontally), and is urged in the accommodation space direction by the spring 17.

It should be noted that while in this embodiment, the fixing member 19 is constructed so as to be able to be driven horizontally, for example, a fulcrum may be provided in a nearly longitudinal central portion of the fixing member 19 so that the fixing member 19 can be rotated about the fulcrum. In this case, the elastic member as the spring 17 has to urge the fixing member 19 in a direction opposite to the exemplified direction (i.e., in a direction of falling apart from the accommodation space 18c). In addition, while in this embodiment, the fixing member 19 is fixed to the heat radiating plate 18 through the elastic member 17, alternatively, the heat radiating plate 18 and the fixing member 19 may also be fixed to the LED case 14 side. In this case, the contact surface 19a contacts the heat radiating plate 18.

Consequently, the fixing member 19 functions as a fixing member for fixing the LED case 14 as the light emitting diode case, and the like since the fixing member 19 has the spring 17 as a member having the elasticity, and the like added thereto. In addition, in this embodiment, the contact surface 19a of the fixing member 19 contacts the lower end of the LED case 14. However, there may also be adopted a construction in which for example, a recess portion is provided in the outer peripheral portion of the LED case 14, and the contact surface 19a contacts the recess portion. Also, the fixing member having the fixing member 19, the spring 17, and the like may also be constructed in the form of a so-called clip which has a shape such as a C-like shape or a ⊐-like shape, and which has the elasticity.

Figure 4A:
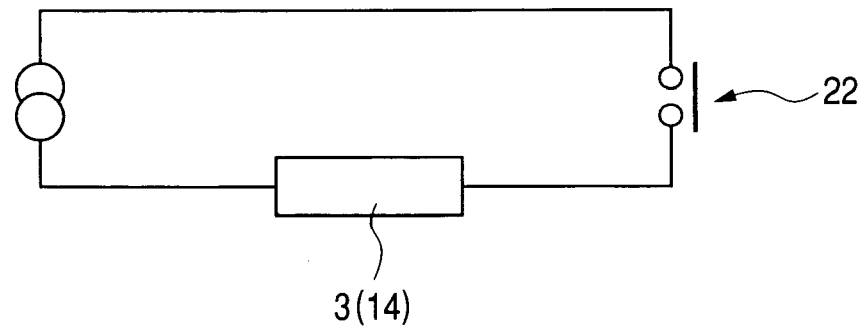
FIG. 4A is a circuit diagram showing a main portion of a configuration of a protection circuit for an LED according to the embodiment of the present invention.

In addition, in this embodiment, the LED case 14, the Peltier element 7, and the heat radiating plate 18 are constructed in the form of the separate constituent elements. Normally, the LED is easy to be damaged due to the calorification. In addition, when a temperature of the LED or the like is intended to be measured, a wiring for the LED and a wiring for a thermometer are necessary. When these wirings are provided integrally with each other, the resultant wiring becomes very complicated. For this reason, in this embodiment, a thermostat 22 is built in the LED case 14 so as to configure a circuit shown in FIG. 4A. The control for turning ON/OFF the Peltier element 7 is carried out by the thermostat 22. In addition, as shown in FIG. 4A, the thermostat 22 is connected in series with the LED 3 to function as a protection circuit as well for the LED 3 in order to prevent the LED 3 from being damaged.

Figure 4B:
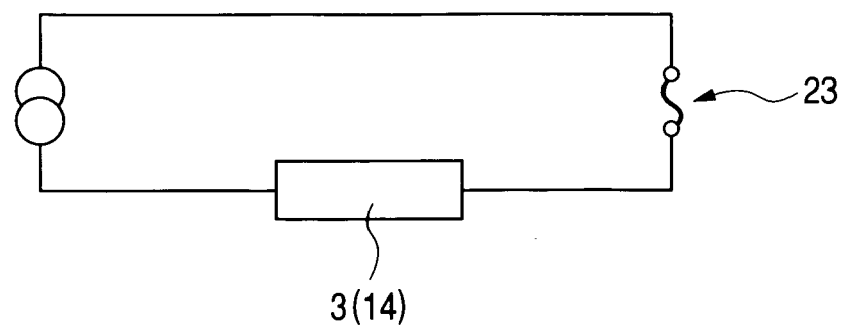
FIG. 4B is a circuit diagram showing a main portion of another configuration of a protection circuit for an LED according to the embodiment of the present invention.

Note that as shown in FIG. 4B, a thermal fuse 23 may be used instead of the thermostat 22 to configure a protection circuit for the LED 3. In this case, the thermal fuse 23 may be built in the LED case 14. In this circuit configuration as well, the thermal fuse 23 functions as the protection circuit for the LED 3, and hence it is possible to obtain the effect of preventing the LED from being damaged. Also, the thermostat 22 or the thermal fuse 23 is built in the LED case 14, resulting in that it becomes possible to reduce the number of wirings relevant to the temperature control. As a result, it is possible to obtain an effect of greatly reducing the number of wirings.

The lighting apparatus 1 constructed as described above is used, whereby the temperature of the camera 20 can be held constant, and hence a subject can be photographed in a fixed color tone. Consequently, even in case of a color image, a clear image of a subject can be stably obtained. In addition, it becomes possible that the individual constituent elements of the lighting apparatus 1 are separately constructed and are combined with one another to construct the lighting apparatus 1. As a result, it becomes possible to provide a miniature and simple lighting apparatus which is capable of being readily fixed to the camera 20, and which is capable of providing the stable quantity of light in correspondence to the photography conditions or the like for a subject to allow a clear color image or the like to be obtained.

Figure 5:
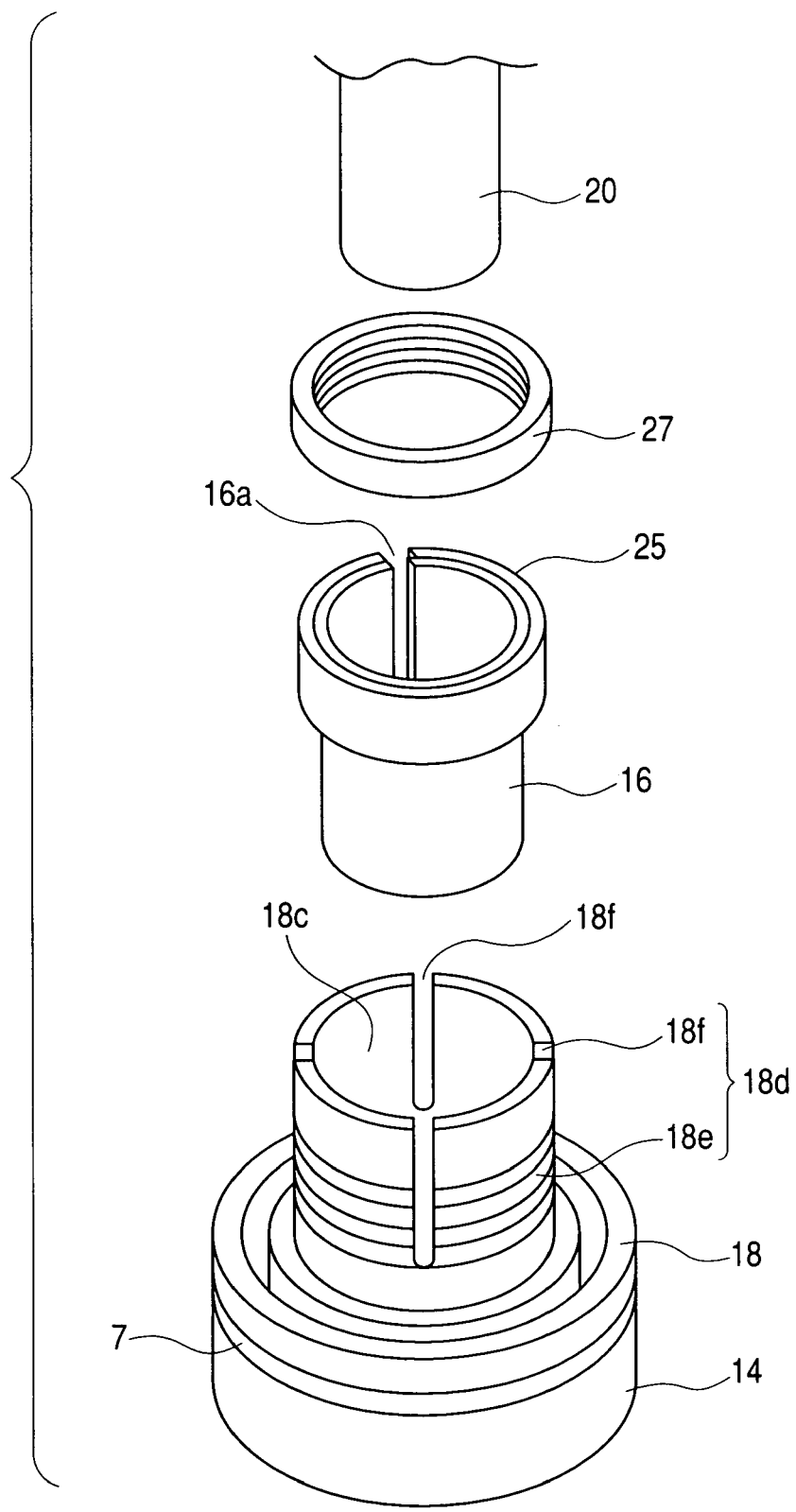
FIG. 5 is an exploded perspective view showing a construction of a change of the embodiment of the present invention.

Next, a change of this embodiment of the lighting apparatus according to the present invention will hereinafter be described with reference to FIG. 5. FIG. 5 is an exploded perspective view showing an assembly state when the lighting apparatus of this change of the above-mentioned embodiment according to the present invention is installed in the camera 20. Note that in this change, the same constituent elements as those in the above-mentioned embodiment are designated with the same reference numerals, and under this state, a description will hereinafter be given. In this change, a description will now be given with respect to a case where an LED case 14, a Peltier element 7, and a heat radiating plate 18 are already integrated with one another by a so-called clip or the like which has a C-like shape or a ⊐-like shape and which has the elasticity using, for example, an adhesive agent having a high thermal conductivity.

Note that the heat radiating plate 18 in this change has a cylindrical projection portion 18d in an upper surface of the plate. The cylindrical projection portion 18d has: slits 18f which are formed in a direction of extension of the cylindrical projection portion 18d; and a tapered male screw 18e which is formed in an outer peripheral portion of the cylindrical projection portion 18d. In addition, an inner diameter of an accommodation space in the LED case 14 is nearly equal to that of an accommodation space in the Peltier element 7. An inner diameter of an accommodation space 18c in the heat radiating plate 18 and its cylindrical projection portion 18d is set larger than that of each of the accommodation spaces of the LED case 14 and the Peltier element 7. A heat insulating member 25 is wound round a portion of a cylindrical thermal transfer member 16 corresponding in position to the heat radiating plate 18.

When the thermal transfer member 16 is inserted into the accommodation space of the LED case 14 and the like based on a relationship among those constituent elements, both the LED case 14 and the Peltier element 7 are brought into tight contact with an outer peripheral portion of the thermal transfer member 16, and the heat radiating plate 18 is nearly brought into tight contact with an outer peripheral portion of the heat insulating member 25. Note that a slit 16a is formed in the thermal transfer member 16 as well in a direction of extension of the thermal transfer member 16.

When the above-mentioned constituent elements are assembled, the thermal transfer member 16 is inserted into the accommodation space of the LED case 14 and the like, a tapered female screw ring 27 is mounted to the cylindrical projection portion 18*d*, and the camera 20 is inserted so as to extend completely through the individual accommodation spaces. Under this state, the tapered male screw 18*e* is tightened with the tapered female screw ring 27. As a result, the width of each of the slit 18*f* and the slit 16*a* is reduced, and thus the LED case 14 and the like, and the thermal transfer member 16 and the like are assembled integrally with one another to be fixed so as to tighten an outer peripheral portion of the camera 20. With this construction, a temperature of the camera 20 can be held more stably since the thermal transfer member 16 covers a wide range of the camera 20 as compared with the case of the above-mentioned embodiment.

The lighting apparatus which is used in the construction permitting an article lighted up with the stable quantity of light to be inspected with a camera has been exemplified as the embodiment of the present invention. However, the implementation of the present invention is not intended to be limited to this technical field. That is, the present invention can also be applied to a construction which requires various light sources each utilizing the directivity or the like of an LED while a use temperature of each light source is held constant. Consequently, each of the above-mentioned accommodation spaces is not limited to a cylindrical shape, and hence can be formed into various shapes such as a square shape. In addition, the idea of the present invention is not applied to only the LEDs, and hence may also be applied to a light source in which the provideable quantity of light is not stabilized unless a use temperature of the light source is stabilized. More specifically, the idea of the present invention can be applied to an apparatus using a light source capable of providing the stable quantity of light by being cooled or heated. In this case, a temperature of the apparatus used together with the light source and provided close to the light source needs to be held constant.

What is claimed is:

1. A lighting unit fixed to an object to have the lighting unit installed therein for lighting up a vicinity of a predetermined focal point, the lighting unit comprising:
   a light emitting diode case having an accommodation space vertically formed and adapted to accommodate the object to have the lighting unit installed therein, and a lower end surface to which a plurality of light emitting diodes able to apply light to the predetermined focal point are fixed;
   a temperature control element having an accommodation space vertically formed and adapted to accommodate the object to have the lighting unit installed therein, and a lower end surface adapted to be brought into tight contact with an upper end surface of the light emitting diode case; and
   a heat radiating member having an accommodation space vertically formed and adapted to accommodate the object to have the lighting unit installed therein, a lower end surface adapted to be brought into tight contact with an upper end surface of the temperature control element, and an upper end surface having a heat radiating construction formed therein, the light emitting diode case, the temperature control element, and the heat radiating member being independent of one another,
   the lighting unit further comprising:
   a fixing member for being urged to at least one of the light emitting diode case and the heat radiating member by an elastic portion, and for contacting the other of the light emitting diode case and the heat radiating member to urge the other in a direction of the one to bring the light emitting diode case, the temperature control element, and the heat radiating member into tight contact with one another when the light emitting diode case, the temperature control element, and the heat radiating member are assembled integrally with one another.

2. A lighting unit according to claim 1, further comprising:
   a thermal transfer member disposed in the accommodation space of at least the temperature control element to contact an end portion of the temperature control element on a side of the accommodation space, and a surface of the object to have the lighting unit installed therein.

3. A lighting unit according to claim 1, wherein one end portion of the fixing member is fixed to at least one of the light emitting diode case and the heat radiating member through a member having the elastic portion, the other end portion of the fixing member has a contact surface having a predetermined angle with respect to a vertical direction, and the contact surface contacts a recess portion provided in one of the other end portion and an outer periphery of the light emitting diode case to thereby apply a vertical urging force to the recess portion.

4. A lighting unit according to claim 1, wherein the light emitting diode case has a protection circuit connected to the light emitting diode.

5. A lighting apparatus fixed to an object to have the lighting apparatus installed therein for lighting up a vicinity of a predetermined focal point, the lighting apparatus comprising:
   a light emitting diode case having an accommodation space vertically formed and adapted to accommodate the object to have the lighting apparatus installed therein, and a lower end surface to which a plurality of light emitting diodes able to apply light to the predetermined focal point are fixed;
   a temperature control element having an accommodation space vertically formed and adapted to accommodate the object to have the lighting apparatus installed therein, and a lower end surface adapted to be brought into tight contact with an upper end surface of the light emitting diode case; and
   a thermal transfer member disposed in the accommodation space of at least the temperature control element to contact an end portion of the temperature control element on a side of the accommodation space, and a surface of the object to have the lighting apparatus installed therein.

* * * * *